(12) United States Patent
Lucassen et al.

(10) Patent No.: US 7,544,503 B2
(45) Date of Patent: Jun. 9, 2009

(54) APPARATUS FOR THE PH DETERMINATION OF BLOOD AND METHOD THEREFOR

(75) Inventors: Gerhardus Wilhelmus Lucassen, Eindhoven (NL); Gerwin Jan Puppels, Rotterdam (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 332 days.

(21) Appl. No.: 10/559,306

(22) PCT Filed: May 27, 2004

(86) PCT No.: PCT/IB2004/050784

§ 371 (c)(1),
(2), (4) Date: Dec. 2, 2005

(87) PCT Pub. No.: WO2004/109267

PCT Pub. Date: Dec. 16, 2004

(65) Prior Publication Data

US 2006/0129036 A1    Jun. 15, 2006

(30) Foreign Application Priority Data

Jun. 6, 2003    (EP) .................................. 03101657

(51) Int. Cl.
    *C12M 1/34* (2006.01)
(52) U.S. Cl. .................................. 435/287.1
(58) Field of Classification Search .................. None
    See application file for complete search history.

(56) References Cited

U.S. PATENT DOCUMENTS

| | | | |
|---|---|---|---|
| 5,355,880 A | 10/1994 | Thomas et al. .............. | 128/633 |
| 5,885,212 A | 3/1999 | Scharlack .................... | 600/322 |
| 6,205,354 B1 | 3/2001 | Gellermann et al. ........ | 600/477 |
| 2002/0156380 A1 | 10/2002 | Feld et al. .................... | 600/473 |

FOREIGN PATENT DOCUMENTS

| WO | WO 99/40411 A1 | 8/1999 |
|---|---|---|
| WO | WO 02/07585 A2 | 1/2002 |
| WO | WO 02/054936 A2 | 7/2002 |
| WO | WO 02/057759 A1 | 7/2002 |

OTHER PUBLICATIONS

Alam et al. Applied Spectroscopy 1998;52(3):393-399.*
Pilotto et al. Lasers Med Sci 2001;16:2-9.*
Bauer et al. "In vivo confocal Raman spectroscopy of the human cornea", Cornea, 1999, 18(4):483-488.*
Alam, M.K., et al.; Characterization of pH Variation in Lysed Blood by Near-Infrared Spectroscopy; 1998; Applied Spectroscopy; 52:393-399.
Caspers, P.J., et al.; In Vivo Confocal Raman Microspectroscopy of the Skin: Noninvasive Determination of Molecular . . . ; 2001; Soc. For Invest. Derm.; 116(3)434-442.

* cited by examiner

*Primary Examiner*—Jon P Weber
*Assistant Examiner*—Bin Shen

(57) ABSTRACT

The present invention relates to a spectroscopic apparatus for non-invasive in vivo analysis of blood and to a corresponding analysis method, in particular for direct determination of the pH value of the blood. From a Raman signal detected from an excited target region containing blood at least one predetermined pH sensitive signal portion is determined, from which the pH value of the blood in the target region by use of a relationship between pH value and one or more band parameters of pH sensitive vibrations of at least one molecule or part of a molecule present in blood, in particular heme vibrations of hemoglobin, is determined.

18 Claims, 2 Drawing Sheets

APPARATUS FOR THE PH DETERMINATION OF BLOOD AND METHOD THEREFOR

Figure 1:
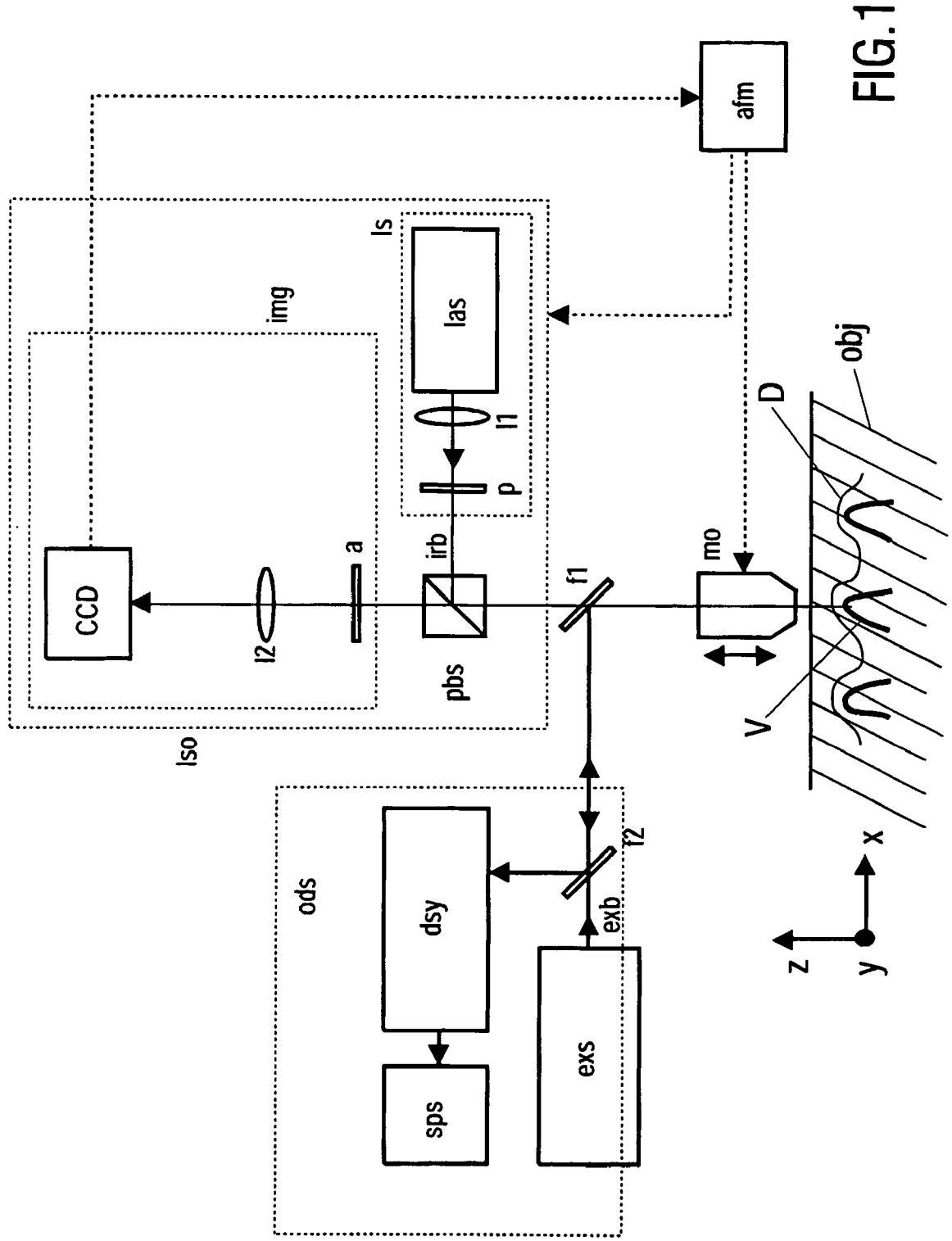

The present invention relates to a spectroscopic analysis apparatus for non-invasive in vivo analysis of blood and to a corresponding analysis method, in particular for the determination of the pH value of the blood.

In general, analysis apparatuses, such as spectroscopic analysis apparatuses, are used to investigate the composition of an object to be examined, e.g. to measure the concentration of various analytes in blood in vivo. In particular, analysis apparatuses employ an analysis, such as a spectroscopic decomposition, based on interaction of the matter of the object with incident electromagnetic radiation, such as visible light, infrared or ultraviolet radiation.

A spectroscopic analysis apparatus comprising an excitation system and a monitoring system is known from U.S. Pat. No. 6,609,015, which is incorporated herein by reference. The excitation system emits an excitation beam to excite a target region during an excitation period. The excitation period and the monitoring period substantially overlap. Hence the target region is imaged together with the excitation, and an image is formed displaying both the target region and the excitation area. On the basis of this image, the excitation beam can be very accurately aimed at the target region.

The analysis method known from U.S. Pat. No. 6,609,015 for simultaneous imaging and spectral analysis of a local composition is done by separate lasers for confocal video imaging and Raman excitation or by use of a single laser for combined imaging and Raman analysis. Orthogonal polarized spectral imaging (OPS IMAGING), which is also described in U.S. Pat. No. 6,609,015 is a simple, inexpensive and robust method to visualize blood vessels close to the surface of organs which can also be used to visualize blood capillaries in the human skin.

The normal pH range in the blood of humans is 7.25-7.45. Outside this range, a person is sick. In critical care units in hospitals doctors use the pH to look at the acid base status of a patient and oxygenation in relation to its ventilation. Normally these parameters are measured in so-called blood gas measurements. A quick and exact determination of the pH value is thus of interest. All known methods to determine the pH value of blood are, however, indirect measurements, i.e. they are based on the relationship between pH, bicarbonate and $pCO_2$. Measuring two of these parameters enables the calculation of the third parameter.

U.S. Pat. No. 5,355,880 describes a reliable noninvasive measurement of blood gases. However, this method is based on absorption differences at 2 or more wavelengths. Furthermore the method measures not only in blood.

It is therefore an object of the present invention to provide an analysis apparatus and a corresponding analysis method for non-invasive in vivo analysis of a patient's blood enabling a direct, quick and exact determination of the pH value of the patient's blood, i.e. without the need to determine bicarbonate or $pCO_2$.

This object is achieved according to the present invention by an analysis apparatus comprising:
- an excitation system for emitting an excitation beam to excite a target region containing blood,
- a detection system for detecting scattered radiation from the target region generated by the excitation beam to obtain a Raman signal,
- a signal processing system for extracting at least one predetermined pH sensitive signal portion from said Raman signal and for determining the pH value of the blood in the target region from said at least one pH sensitive signal portion by use of a relationship between pH value and one or more band parameters of pH sensitive vibrations of at least one molecule or part of a molecule present in blood.

The present invention is based on the idea to exploit a relationship between pH value and a band parameter of vibrations of a blood molecule. To exploit this relationship a Raman signal of in vivo blood is measured non-invasively. From this Raman signal at least one pH sensitive signal portion is selected for which the given relationship can be used. Thus, pH sensitive spectral characteristics of the blood sample are determined from which the pH value can be directly derived.

According to the present invention a direct non-invasive measurement of the pH value in blood enables a continuous and immediate monitoring in critical care situations, which are useful for e.g. patients with respiratory or metabolic disorders in the ICU where the condition of the patient can change rapidly. Further, this method can be applied to neonates who only have a low amount of blood. The replacement of non-direct methods may also reduce costs, and finally a reduced risk of infections can be achieved.

According to a preferred embodiment of the invention the signal processing means is adapted for determining the pH value by use of a given relationship between pH value and band position, band intensity, band polarisation ratio, band width and/or band shape. This means that at best only one of these parameters needs to be determined from the pH sensitive signal portion of the detected Raman signal. Since at different wavelengths of the Raman signal relationships between pH value and different band parameters exist it also depends on the intensity of the obtained Raman signal, the magnitude of its pH sensitivity, as well as on the interfering signal from other molecules in the measurement volume, which band parameter and which relationship shall be exploited according to the invention in order to obtain the pH value of the blood. pH sensitivity can furthermore be optimized by proper choice of the excitation wavelength. In that way it is possible to enhance pH sensitive hemoglobin bands over other signal contributions.

According to a preferred embodiment a relationship between pH value and one or more band parameters of heme vibrations of hemoglobin is exploited in order to determine the pH of the blood since the pH sensitivity of the hemoglobin Raman signal is largest. But there are other molecules with pH sensitivity in blood, which can be exploited as well. It is, for instance, known that molecules that can form H-bridges can be pH sensitive.

Preferably only one or more Raman signal portions of heme vibrations of hemoglobin are detected at all instead of detecting a broadband Raman signal and thereafter extracting predetermined pH sensitive signal portions therefrom. This leads to a simpler, less expensive instrument, comprising just a few optical measurement channels.

It is further preferred to detect only scattered radiation from a target region containing essentially whole blood or red blood cells which contain hemoglobin which best enables the application of the given relationship between pH value and band parameter. However, it is generally also possible to perform a measurement on blood plasma or blood serum.

According to a further embodiment a monitoring system for imaging the target region and a focussing system for focussing the excitation system, the detection system and the monitoring system on the target region, in particular on a blood vessel, are provided. By use of the focussing system the excitation beam can be exactly aimed at the object of interest, i.e. a blood vessel. Manual or automatic focussing techniques can be used. To enable a continuous focussing during the whole analysis, which also compensates for movements of the patient automatic focussing techniques are preferred.

It is further advantageous if the signal processing system is adapted for checking if the at least one pH sensitive signal portion includes interferences from other analytes, such as lactate and lactate acidosis or oxygenation, and for removing such interferences. This can be achieved by selection of the wavenumber regions used in the analysis or by mathematical modelling of the pH sensitive signal portion and the signal portion that is sensitive for the analytes, e.g. via spectra processing (e.g. filtering and multivariate spectral analysis). Removing the interferences improves the determination accuracy of the pH value with less error and will yield higher pH sensitivity.

According to another aspect of the invention the excitation system is optimised in the sense of emitting an excitation beam at a wavelength which is optimised such that the at least one pH sensitive signal portion shows an optimum pH sensitivity. Such an optimised excitation wavelength can be found by collecting blood spectra of different pH at different wavelengths and analysing the pH sensitive signal portion. The optimum value for the excitation wavelength is characterised by yielding minimal errors in prediction of the pH in an independent test set of blood spectra.

Preferred band positions at which the Raman signal shows pH sensitivity are defined in claim 9. At those band positions the relationship between pH value and the wavenumber has been found which allows an exact determination of the pH value if the wavenumber is determined from the Raman signal. Of course, these band positions are not necessarily the only band positions, other band positions may be found as well.

The pH influence on the Raman spectra is also revealed in the polarization characteristics of the vibrational bands of the heme group. The depolarisation ratio, i.e. the ratio of the Raman intensity with perpendicular analyser setting to the intensity with parallel analyser setting with respect to the incoming polarisation orientation, has been measured as a function of the excitation wavelength. These so-called depolarisation ratio excitation profiles clearly show pH sensitivity for different band positions, in particular for the same band positions as defined in claim 9. Since measuring a number of excitation wavelengths is not very practical, the depolarisation ratio is preferably measured at a well chosen (one or more) excitation wavelength(s). An appropriate embodiment of the analysis apparatus according to the invention is defined in claim 10, which makes use of the depolarisation ratio for determining the pH value in blood.

The pH dependency of the Raman spectra of blood can also be determined by application of multivariate statistical calibration techniques, such as Partial Least Squares (PLS). PLS uses a spectral model data set of selected blood samples with known pH values, determined with a reference analysis method. This model data set should include all possible spectral variation (both due to pH and interfering contributions of other analytes) that can be encountered in practice to yield a valid model. Multivariate analysis of the covariance between the spectra and the reference values is used to find the spectral regression vector that correlates with the reference pH values. Projection of a new spectrum onto the regression vector then yields the predicted pH value for that new spectrum. It is advantageous to use non-linear PLS techniques. Also artificial neural networks can be designed and trained by means of model data to predict the pH of a new blood sample.

Figure 2:
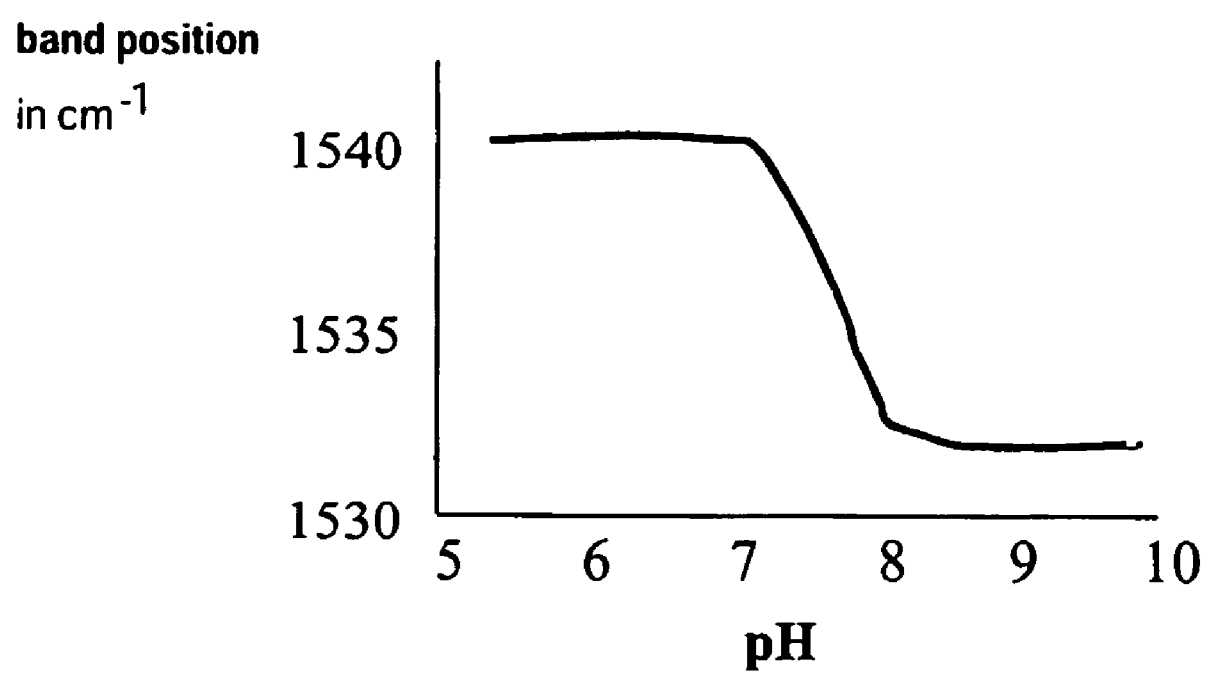

The invention will now be explained in more detail with reference to the drawings in which Brief Description of the Drawing FIG. 1 shows a graphic representation of a preferred embodiment of an analysis system according to the present invention and FIG. 2 shows the relationship between pH value and wavenumber at a particular band position.

FIG. 1 is a graphic representation of a preferred embodiment of an analysis system in accordance with the invention. The analysis system includes an optical monitoring system (lso) for forming an optical image of the object (obj) to be examined. In the present example the object (obj) is a piece of skin of the forearm of the patient to be examined. The analysis system also includes a multi-photon, non-linear or elastic or inelastic scattering optical detection system (ods) for spectroscopic analysis of light generated in the object (obj) by a multi-photon or non-linear optical process. The example shown in FIG. 1 utilises in particular an inelastic Raman scattering detection system (dsy) in the form of a Raman spectroscopy device. The term optical encompasses not only visible light, but also ultraviolet radiation and infrared, especially near-infrared radiation.

The monitoring system (lso) comprises a monitoring beam source (ls) for emitting a monitoring beam (irb) and an imaging system (img) for imaging the target region, e.g. a blood vessel (V) in the upper dermis (D) of the patient's forearm (obj). The monitoring beam source (ls) in this example comprises a white light source (las), a lense (l1) and an interference filter (not shown) to produce light in the wavelength region of 560-570 nm. Further, a polarizer (p) for polarizing the monitoring beam (irb) is provided. The monitoring beam source (ls) is thus adapted for orthogonal polarized spectral imaging (OPS imaging).

In OPS imaging polarized light is projected by a microscope objective (mo) through a polarizing beam splitter (pbs) onto the skin (obj). Part of the light reflects directly from the surface (specular reflection). Another part penetrates into the skin where it scatters one or more times before it is absorbed or is re-emitted from the skin surface (diffuse reflection). In any of these scattering events the polarization of the incident light is slightly changed. Light that is directly reflected or penetrates only slightly into the skin will scatter only one or a few times before it is re-emitted, and will mostly retain its initial polarization. On the other hand, light that penetrates more deeply into the skin undergoes multiple scattering events and is completely depolarized before re-emitted back towards the surface.

When looking at the object (obj) through a second polarizer or analyser (a), oriented precisely orthogonal to that of the first polarizer (p), light reflected from the surface or the upper parts of the skin is largely suppressed, whereas light that has penetrated deep into the skin is mostly detected. As a result the image looks as if it were back-illuminated. Because wavelengths below 590 nm are strongly absorbed by blood, the blood vessels appear dark in the OPS image.

Generally, an image is obtained using a monochrome CCD camera. Blood vessels are separated from other absorbing structures be means of size, shape and movement of blood cells. The imaging system (img) used in the present embodiment comprises an analyser (a) mentioned above for allowing only light having a polarization orthogonal to the light of the polarized monitoring beam (irb) to pass which is reflected back through the polarizing beam splitter (pbs) from the object (obj). Said light is further focused by a lens (l2) onto the CCD-camera (CCD).

The Raman spectroscopy device (ods) comprises an excitation system (exs) for emitting an excitation beam (exb) and a detection system (dsy) for detection of Raman scattered signals from the target region. The excitation system (exs) can be constructed as a diode laser, which produces the excitation beam in the form of an 785 nm infrared beam (exb). Of course other lasers can be used as excitation system as well. A system of mirrors and, for instance, a fibre conduct the excitation beam (exb) to a dichroic mirror (f1) for conducting the excitation beam (exb) along the monitoring beam (irb) to the microscope objective (mo) for focusing both beams onto the object (obj).

The dichroic mirror (f1) also separates the return (monitoring) beam from scattered Raman signals. While the reflected monitoring beam is transmitted to the imaging system (img), elastically scattered light and inelastically scattered (Raman) light from the object is reflected at the dichroic mirror (f1) and conducted back along the light path of the excitation beam. Inelastically scattered Raman light is then reflected by an appropriate filter (f2) and directed along the Raman detection path in the detection system (dsy) to the input of a spectrometer with a CCD detector. The spectrometer with the CCD detector is incorporated into the detector system (dsy), which records the Raman spectrum for wavelengths that are smaller than approximately 1050 nm. It should be notet that this limitation is at present due to limited quantum efficiency at this IR spectral side in CCD cameras. With technical improvements in CCD cameras this number 1050 nm can probably be increased to higher wavelengths.

The output signal of the spectrometer with the CCD detector represents the Raman spectrum of the Raman scattered infrared light. In practice this Raman spectrum occurs in the wavelength range beyond 800 nm, depending on the excitation wavelength. The signal output of the CCD detector is connected to a spectrum display unit, for example a workstation that displays the recorded Raman spectrum on a monitor. Also a calculation unit (e.g. a workstation) is provided to analyse the Raman spectrum and calculate the concentration of one or more analytes.

Regarding further details of the analysis apparatus in general and the function thereof reference is made to the above mentioned WO 02/057759 A1.

To achieve continuous auto-focusing of the confocal Raman system (ods) in a blood vessel (V) auto-focussing means (afm) are provided. Such auto-focussing is required since patients can move during a blood analysis in lateral (z) as well as in transversal (x, y) directions. Therefore, continuous determination and adjustment of the optimal location of the confocal detection centre is required. Transversal movements can be easily detected by the imaging system, whereas axial movements are much more difficult to detect. These auto-focussing means (afm) ensure that the optical detection system (ods) and the monitoring system (lso) are continuously and optimally focussed on the object of interest, e.g. a selected blood vessel (V), during recording of the blood spectra. Many different techniques can be used therefore which will not be explained here in detail. Alternatively, manual auto-focussing means can be used instead, by which a user can manually change the focussing of the microscope objective (mo) to find the best focussing position.

In order to determine the pH value of the blood, from which a Raman signal has been detected by the detection system (dsy), a signal processing system (sps) is provided in the optical detection system (ods). Therein at least one signal portion is extracted from the whole Raman signal, which shows a significant pH sensitivity allowing determination of the pH value therefrom. From this at least one signal portion at least one predetermined band parameter is determined, such as band position, band intensity, band polarisation ratio, band width and/or band shape or a combination of these. Which band parameter is actually determined depends on the fact, for which parameter a relationship between the pH value to be determined and band parameter is known for the extracted signal portion of the Raman signal.

For instance, it has been found that the sensitive Raman bands in the heme group are 1378 cm$^{-1}$, 1506 cm$^{-1}$ and 1638 cm$^{-1}$ related to the vibrational band $\mu_{Fe-His}$ of the central Fe atom connected to the Histidin group of the heme protein hemoglobin. The influence of a changed pH to the position of porphyrin bands has also been measured in the past showing a pH dependence of the wavenumber of ferrous alkylated cytochrome c (Parker, Biological applications of IR and Raman, Chapter 6, Porphyrins and Hemoproteins, page 276, 1982). It has been found that also human blood shows a similar pH dependence of the wavenumber at the above mentioned band positions so that in a preferred embodiment the band position, or more particularly the wavenumber, is determined from the extracted signal portion of the Raman signal from which then by use of the given relationship the pH value can be determined. Such a pH dependence of the wavenumber and a band position around 1535 cm$^{-1}$ for blood is schematically shown in FIG. 2.

In order to directly determine the pH value of blood by use of a detected Raman signal besides measuring the band parameters of the pH sensitive heme vibrations other ways are possible as well, such as measuring the polarisation characteristics of the pH sensitive heme vibrations. Further, a multivariate statistical analysis of whole blood spectra can be performed and train prediction models on blood samples of known pH can be used as described above. Further, the embodiment of an analysis apparatus shown in FIG. 1 is only one example of a particular layout. Of course, other embodiments of an analysis apparatus, for instance having other embodiments of monitoring systems, e.g. adapted for monochromatic, bichromatic or multichromatic imaging, can be used as well.

In summary, the following , steps or considerations can be taken to perform a non-invasive in vivo analysis of blood for determining the pH value:

1. recognize that certain heme band positions shift in dependence on pH;
2. need to derive pH from band (shifted) positions $\Omega$ of heme vibrations in blood;
3. therefore need to inverse the relationship of $\Omega=\Omega(\text{ph})$ to $\text{pH}=\text{pH}(\Omega)$;
4. in blood of healthy people the pH range is small (pH=7.25-7.45), pH<7.25 is danger for changed cell metabolism, and medical action is needed;
5. find band positions of pH sensitive heme vibrations that show a change in this range;
6. recognize that this change in band positions is in a practically measurable wavenumber range (1-2 cm$^{-1}$);
7. need to measure band positions of heme with high enough accuracy (0.02 to 0.1 cm$^{-1}$) to get relevant accuracy in pH change;
8. do the experiment on in vivo blood: measure Raman of heme vibrations of hemoglobin in in vivo blood;
9. the ideal way to do this is non-invasively: find blood vessels in the skin and measure directly in the blood vessel;
10. check if there are interferences from other analytes (e.g. lactate and lactate acidosis, oxygenation, etc), and if so remove them;
11. optimize signals by finding the right excitation wavelength(s) to do the measurement.

The invention allows a direct, quick, accurate and non-invasive determination of the pH value of blood without the need to separately determine pCO$_2$ or bicarbonate.

The invention claimed is:

1. A spectroscopic analysis apparatus for non-invasive in vivo analysis of blood comprising:
    an excitation system for emitting an excitation beam to excite a target region containing a blood vessel, said excitation system configured to emit an excitation beam having a predetermined polarization orientation;
    a detection system for detecting scattered radiation from blood in the blood vessel in the tar et re ion generated b the excitation beam to obtain a Raman signal;
    a signal processing system for extracting at least one predetermined pH sensitive signal portion from said Raman signal and for determining a depolarization ratio from said at least one pH sensitive signal portion of said Raman signal and for determining the pH value of the blood in the target region from said depolarization ratio by use of a relationship between pH value and depolarization ratio of vibrations of one or more molecules at excitation wavelengths included in said at least one pH sensitive signal portions;
    a monitoring system for imaging the target region; and
    a focusing system for focusing the excitation system, the detection system and the monitoring system on the target region.

2. The analysis apparatus as claimed in claim 1, wherein said detection system is adapted to detect scattered radiation from the target region containing essentially whole blood or red blood cells.

3. The analysis apparatus as claimed in claim 1, further including:
    a light source which provides a light beam for the monitoring system.

4. The analysis apparatus as claimed in claim 3, further including:
    a microscope objective which focuses the excitation beam and the monitoring system light source beam on the target region.

5. The analysis apparatus as claimed in claim 1, further including:
    a filter for suppressing directly reflected light from reaching the monitoring system and contributing to the imaging of the target region.

6. A spectroscopic analysis apparatus for non-invasive in vivo analysis of blood comprising:
    an excitation system for emitting an excitation beam to excite a target region containing blood;
    a detection system for detecting scattered radiation from the target region generated by the excitation beam to obtain a Raman signal;
    a signal processing system for extracting at least one predetermined pH sensitive signal portion from said Raman signal and for determining the pH value of the blood in the target region from said at least one pH sensitive signal portion by use of a relationship between pH value and one or more band parameters of pH sensitive vibration of at least one molecule or part of a molecule present in blood;
    a monitoring system for imaging the target region;
    a focusing system for focusing the excitation system, the detection system and the monitoring system on the target region on a blood vessel; and
    an auto focus system which continually adjusts a confocal center of the excitation beam.

7. The analysis apparatus as claimed in claim 6, wherein said signal processing system is adapted for determining the pH value by use of a given relationship between pH value and band position, band intensity, band polarization ratio, band width and/or band shape.

8. The analysis apparatus as claimed in claim 6, wherein said signal processing system is adapted for determining the pH value by use of a relationship between pH value and one or more band parameters of pH sensitive heme vibrations of hemoglobin.

9. The analysis apparatus as claimed in claim 8, wherein said detection system is adapted to detect only one or more Raman signal portions of the heme vibrations of hemoglobin.

10. The analysis apparatus as claimed in claim 6, wherein said signal processing system is further adapted for checking if the at least one pH sensitive signal portion includes interferences from other analytes and for removing such interferences from the at least one pH sensitive signal portion.

11. The analysis apparatus as claimed in claim 6, wherein said excitation system is adapted for emitting an excitation beam at a wavelength which is optimized such that the at least one pH sensitive signal portion shows an optimum pH sensitivity.

12. The analysis apparatus as claimed in claim 6, wherein said signal processing system is adapted for extracting at least one predetermined ph sensitive signal portion from said Raman signal at a band position of substantially 1378 cm$^{-1}$, 1506 cm$^{-1}$ or 1638 cm$^{-1}$.

13. The analysis apparatus as claimed in claim 6, wherein the excitation system emits an excitation beam having a predetermined polarization orientation and wherein the signal processing system determines a band parameter of vibrations of one or more blood molecules in the target region from the Raman signal and determines the pH value of the blood in the target region from the determined band parameter.

14. The analysis apparatus as claimed in claim 13, wherein the band parameter includes depolarization ratio excitation profiles at a preselected excitation wavelength.

15. A spectroscopic analysis apparatus including:
    an optical detection system including:
        an excitation s stem configured to emit an excitation beam to excite blood in a blood vessel below a surface of a subject,
        a detection system configured to detect scattered radiation from the blood in the blood vessel to generate a Raman signal,
        a signal processing system configured to determine a pH value of the blood in the blood vessel from the Raman signal;
    an optical monitoring system including:
        an optical light source configured to emit a monitoring beam that penetrates to the blood vessel,
        a camera configured to receive the monitoring beam from the blood vessel and form an image of the blood vessel;
    a microscope object which focuses the excitation and monitoring beams into the subject, the microscope object hem controllable in accordance with the image to focus at least the excitation beam on the blood vessel; and
    an auto focus mechanism connected with the camera and the microscope object to adjust the focus of the microscope object to maintain a confocal detection center of the excitation beam focused on the blood vessel when the subject moves.

16. The analysis apparatus as claimed in claim 15, further including:

a filter for suppressing directly reflected light from reaching the monitoring system and contributing to the imaging of the blood vessel.

17. The analysis system as claimed in claim 15, wherein the autofocus mechanism is further configured to track the blood vessel through three spatial dimensions of motion.

18. The analysis apparatus as claimed in claim 15, wherein the excitation system emits an excitation beam having a predetermined polarization orientation and wherein the signal processing system determines a depolarization ratio of one or more molecules in the blood in the blood vessel at blood excitation wavelengths from the Raman signal and determines the pH value of the blood in the blood vessel from the determined depolarization ratio.

\* \* \* \* \*